(12) United States Patent  
Owen (10) Patent No.: US 11,898,959 B2  
(45) Date of Patent: Feb. 13, 2024

(54) SOLIDS ANALYSIS USING RAMAN SPECTROSCOPY

(71) Applicant: Harry Owen, Frankiln, MI (US)

(72) Inventor: Harry Owen, Frankiln, MI (US)

( * ) Notice: Subject to any disclaimer, the term of this patent is extended or adjusted under 35 U.S.C. 154(b) by 0 days.

(21) Appl. No.: 17/543,401

(22) Filed: Dec. 6, 2021

(65) Prior Publication Data

US 2022/0178830 A1 Jun. 9, 2022

Related U.S. Application Data

(60) Provisional application No. 63/122,261, filed on Dec. 7, 2020.

(51) Int. Cl.
*G01N 21/65* (2006.01)
*G01N 33/15* (2006.01)

(52) U.S. Cl.
CPC .......... *G01N 21/658* (2013.01); *G01N 33/15* (2013.01); *G01N 2201/06113* (2013.01)

(58) Field of Classification Search
CPC ................. G01N 21/658; G01N 33/15; G01N 2201/06113
See application file for complete search history.

(56) References Cited

U.S. PATENT DOCUMENTS 7,148,963 B2 * 12/2006 Owen ................... G01N 21/645
356/301
8,054,463 B2 * 11/2011 Morris ................. G01N 21/474
356/326

8,085,396 B2 * 12/2011 Matousek .............. A61B 5/417
250/221
2005/0010130 A1 * 1/2005 Morris ................. A61B 5/4514
600/562

(Continued)

OTHER PUBLICATIONS

Boere, I. A., et al. "Use of fibre optic probes for detection of Barrett's epithelium in the rat oesophagus by Raman spectroscopy." Vibrational Spectroscopy 32.1 (2003): 47-55 (Year: 2003).*

(Continued)

*Primary Examiner* — Kevin Quarterman
*Assistant Examiner* — Roberto Fabian, Jr.
(74) *Attorney, Agent, or Firm* — Fishman Stewart PLLC (57) ABSTRACT

Raman systems and methods use advantages offered by increased laser mobility/path length and photon migration to analyze diffusively scattering solids, including pharmaceuticals. A collimated laser excitation beam having a first diameter induces from a sample a backscattered collimated Raman collection beam with a second diameter. The collimated laser excitation beam and the collimated Raman collection beam form a counter-propagating collimated optical path, and the collimated laser excitation beam is preferably smaller in diameter than the diameter of the backscattered collimated Raman beam. The collection beam to a spectrograph for Raman analysis of the sample. A Raman calibration standard may be placed in the collimated optical path, and/or the sample may be supported in a reflective holder that may be at least partially spherical and/or may form part of a multi-well plate. The counter-propagating collimated optical path may be contained within a Raman microscope.

23 Claims, 7 Drawing Sheets

(56) References Cited

U.S. PATENT DOCUMENTS

2005/0029458 A1* 2/2005 Geng ................ H04N 5/23238
  250/347
2018/0143415 A1* 5/2018 Hollricher ............ G02B 21/006

OTHER PUBLICATIONS

Choquette, S. J., et al. "Relative intensity correction of Raman spectrometers: NIST SRMs 2241 through 2243 for 785 nm, 532 nm, and 488 nm/514.5 nm excitation." Applied spectroscopy 61.2 (2007): 117-129 (Year: 2007).*

"A stainless steel multi-well plate (SS-MWP) for high-throughput Raman analysis of dilute solutions." Journal of Raman Spectroscopy 41.10 (2010): 1266-1275 (Year: 2010).*

Ian R. Lewis and Mary L. Lewis, Fiber-optic Probes for Raman Spectrometry, the Handbook of Vibrational Spectroscopy in 2006 by John Wiley & Sons, Ltd.

* cited by examiner

SOLIDS ANALYSIS USING RAMAN SPECTROSCOPY

REFERENCE TO RELATED APPLICATIONS

This application claims priority to, and the benefit of, U.S. Provisional Patent Application Ser. No. 63/122,261, filed Dec. 7, 2020, the entire content of which is incorporated herein by reference.

FIELD OF THE INVENTION

This invention relates generally to Raman spectroscopy and, in particular, to the analysis of diffuse solids, including pharmaceuticals.

BACKGROUND OF THE INVENTION

Techniques such as Raman spectroscopy identify and measure the molecular constituents and structural formation of a sample. Raman, for example, relies on inelastic scattering of monochromatic light, usually from a laser in the visible, near infrared, or near ultraviolet range to generate a Raman spectrum.

Raman spectroscopy has been developed from a microscope-based identification tool into an attractive probe-based or analyzer-based measurement tool for the development and quality control of solids, including pharmaceutical products such as tablets. As a measurement tool, Raman spectrum from a representative volume of the sample is critical if the active pharmaceutical content (API) in the sample is to be measured accurately and with acceptable precision at low dosage levels.

Different surface-based sampling configurations, including focused multiple single points, circular point, and area by simultaneously rotating and translating a focused point exposure on the tablet surface have been described[1]. Using backscattered collection of the Raman spectra demonstrated some success on relatively high dosage formulations. Lower dosage formulations would experience under sampling or sub-sampling by use of surface-based focused point sampling configurations.

Representative sampling for uncoated pharmaceutical tablets was demonstrated by the introduction of the PhAT probe by Kaiser Optical Systems. By increasing the focused spot size onto the sample from 100-500 microns to 6 mm, a representative volume of the sample was obtained but with a surface layer bias[2]. The surface bias due to the focusing properties of this probe are demonstrated positively by the application to monitor and measure the process of real-time coating of pharmaceutical tablets with controlled release coatings and coatings containing the active ingredient[3].

Surface layer bias and subsampling can be practically eliminated by using a transmission geometry in which Raman signals are collected on the opposite side of the laser illumination[4]. This technique is well suited for non-absorbing or weakly absorbing diffusely scattering samples providing representative spectroscopic information from sample throughout its depth[5].

SUMMARY OF THE INVENTION

Solid samples, including pharmaceutical tablets and products containing highly absorbing components, limit the applicability of the transmission geometries in Raman analysis. To overcome these deficiencies, this invention utilizes collimated light configurations that combine both backscattered and reflected Raman signals, offering improved performance over transmission geometries. In broad and general terms, the invention utilizes the advantages offered by the effects of increased laser mobility/path length and photon migration within diffusively scattering solids. In accordance with this invention, the collimated backscatter geometry alone remains sufficient to generate a representative Raman spectrum without interference from a surface coating.

In preferred embodiments, a counter-propagating optical path containing both the excitation and collection beams, extends directly to and from the surface of a solid sample with no intervening focusing or re-collimating optical components. A method of performing Raman analysis of a solid sample, including a diffusively scattering solid sample, comprises the step of directing a collimated laser excitation beam onto a solid sample so as to induce from the sample a backscattered collimated Raman collection beam, thereby forming the counter-propagating collimated optical path. In some embodiments, the collimated laser excitation beam may be smaller in diameter than the diameter of the backscattered collection beam.

The system and method may include positioning a Raman calibration standard in the collimated optical path, and using the Raman analysis of the sample for calibration purposes. The standard may be a $CaF_2$ or other wavenumber calibration standard (i.e., diamond, sapphire, etc.), or a NIST standard for intensity calibration. In certain preferred embodiments the sample may be supported in a reflective holder. The reflective holder may include a gold, silver or copper surface, and the shape of the holder may be at least partially spherical. The reflective holder may form part of a multi-well plate.

The counter-propagating collimated optical path may be contained within a Raman microscope. To ensure that the counter-propagating collimated optical path extends directly to and from the sample, the microscope may be designed without objective optics, or existing objective optics may be removed and/or replaced with a window. A calibration material may be used as the window, as Raman microscopes are often subject to drift due to temperature or other environmental/operational considerations.

The sample may be a pharmaceutical, such as a tablet, capsule, gelcap, a coated product, or a packaged product. The method may be used to determine a dosage formulation; the properties of the tablet in polymorph form, hydrated form, solvate form, or salt form; or characteristics associated with a highly absorbent or thick pharmaceutical dosage.

Apparatus for performing a Raman analysis of a solid sample, including a diffusively scattering solid sample, comprises a source of a collimated laser excitation beam, and apparatus for directing the collimated laser excitation beam onto the surface of a solid sample so as to induce from the sample a backscattered collimated collection, such that the collimated laser excitation beam and the collimated Raman collection beam form a counter-propagating collimated optical path directly to and from the surface of the sample. The collection beam is directed to a spectrograph for performing a Raman analysis of the sample.

The system and method may be operated within any applicable laser wavelength range, from UV to NIR. Additional apparatus is described, and various examples of use are presented.

DETAILED DESCRIPTION OF THE INVENTION

In the context of Raman analysis, this invention broadly utilizes the advantages offered by the effects of increased laser mobility/path length and photon migration within diffusively scattering solids. Collimated light configurations combine both backscattered and reflected Raman signals, offering improved performance over transmission geometries. Thick pharmaceutical products, or products containing highly absorbing components, limit the applicability of the transmission geometry. However, in accordance with this invention, the collimated backscatter geometry alone remains sufficient to generate a representative Raman spectrum without interference from a surface coating.

Figure 1A:
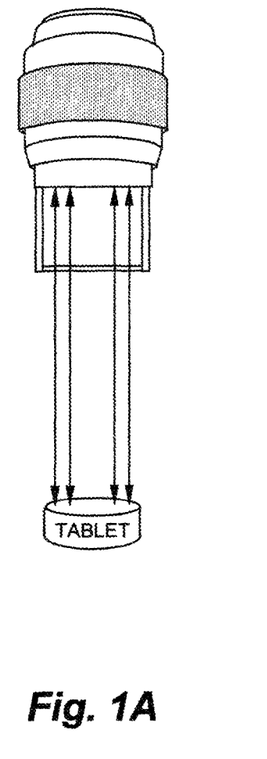
FIG. 1A depicts an optical configuration based on a collimated laser excitation beam and a backscattered collimated Raman collection beam for both measurement and calibration of a solid material such as a pharmaceutical tablet.

The invention recognizes the benefits of using an optical configuration based on a collimated laser excitation beam and a backscattered collimated Raman collection beam for both measurement and calibration (FIG. 1A). The collimated laser excitation beam, unlike surface-focused schemes, efficiently passes through surface coatings on tablets, and generates a representative measurement from the bulk of the tablet.

Figure 1B:
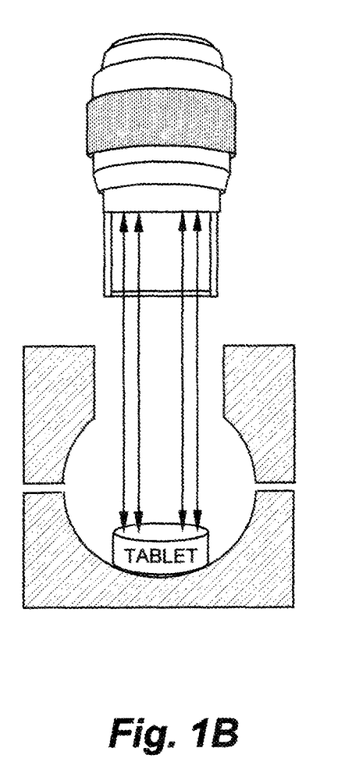
FIG. 1B shows that by enclosing the tablet within a polished, highly reflecting sample holder, the laser path length is extended further by diffuse scattering within the sample, thereby generating an enhanced Raman signal.
Figure 1C:
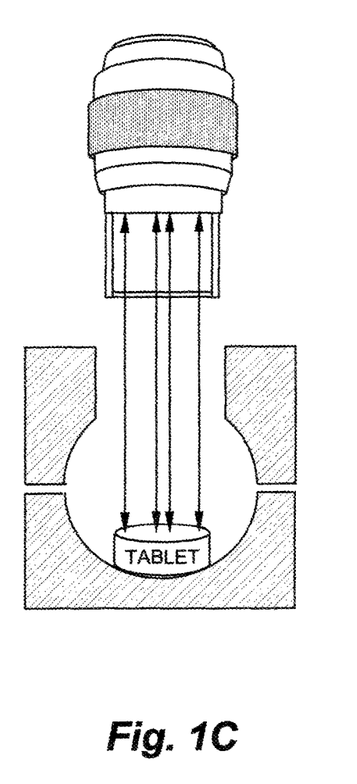
FIG. 1C shows that by reducing the diameter of the collimated laser excitation beam with respect to the backscattered collimated Raman collection beam, the path length of the laser is increased further due to positive biasing of the center of the tablet, thereby further enhancing the returning Raman signal.

By enclosing the tablet within a polished, highly reflecting sample holder, the laser path length is extended further by diffuse scattering within the sample, generating an enhanced Raman signal (FIG. 1B). A gold coating is preferred at 785 nm laser excitation wavelengths, as it will significantly increase the reflectivity from around 35% for stainless steel to over 90% for gold plating. A silver coating is preferred for 514 nm and 532 nm lasers with over 90% reflectivity. By reducing the diameter of the collimated laser excitation beam with respect to the backscattered collimated Raman collection beam, the path length of the laser is increased further due to positive biasing of the center of the tablet, thereby enhancing the returning Raman signal (FIG. 1C).

In a preferred embodiment, the reflecting sample holder is at least partly spherical. The base of the spherical holder supporting a pharmaceutical product should be flat, however, to increase the retroflection of the laser and Raman signal, since scattering is often strongly biased towards the forward direction. Off-axis laser and Raman reflections from the sides of the polished sample holder are directed back into the pharmaceutical product or formulation, extending the laser path length, further enhancing the returning representative Raman signal.

Incorporating a Raman Calibration Standard (e.g., $CaF_2$, Diamond, Sapphire) into the collimated light path will generate a reference Raman spectral band (e.g., 321.0 wavenumbers for $CaF_2$), allowing one to use real-time wavenumber calibration to wavenumber stamp each collected Raman spectra to correct for the gradual laser and spectrograph drift experienced by most Raman instruments. Raman microscopes are particularly sensitive to changes in room temperature degrading wavenumber precision.

Enclosing the Raman Calibration Standard and a NIST intensity calibration standard into individual calibration accessories enables the user to benefit from the combined use of a collimated laser beam and backscattered collimated light collection to generate representative Raman and fluorescence signals, while eliminating the problem of unwanted stray light and improving the placement accuracy of both types of reference optic with respect to the incident laser beam. This option is preferred when the band or bands from the Raman Calibration Standard interferes with the Raman spectral bands generated by the sample.

A significant commercial benefit of using the disclosed Raman collection and Raman calibration configurations is that existing research and analytical Raman microscopes can be easily upgraded to add quantitative measurement capability in addition to their existing qualitative capability.

FIG. 1A is schematic drawing showing overlapping collimated laser input and collimated Raman backscatter collection and Raman Calibration Standard $CaF_2$ optic as the window. FIG. 1B is shows overlapping collimated laser input and collimated Raman backscatter collection and Raman Calibration Standard $CaF_2$ optic as the window with a highly reflecting gold coated spherical sample holder to enhance the Raman signal. FIG. 1C depicts a smaller diameter collimated laser input and larger collimated Raman backscatter collection.

A Raman Calibration Standard $CaF_2$ optic employed as the window, with a highly reflecting gold coated spherical sample holder, further enhance Raman signal by biasing the reduced diameter laser beam into the center of the solid sample. Reducing the diameter of the incident collimated laser beam increases the laser intensity in the center of the tablet increasing the laser mobility or the laser path length as it is scattered within the diffuse scattering solid.

Figure 2:
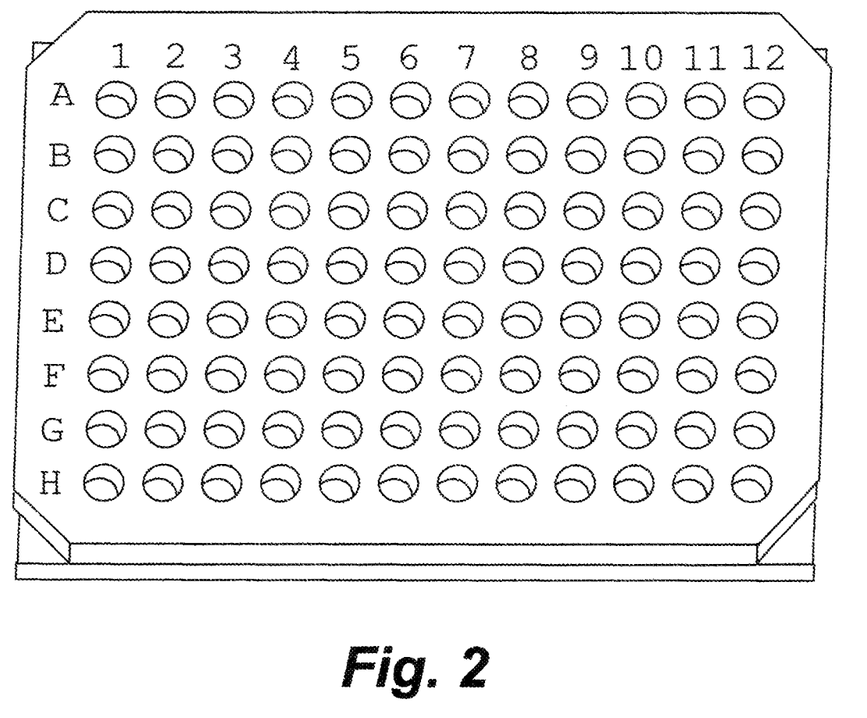
FIG. 2 illustrates an electropolished stainless-steel well plate that reduces unwanted Raman background signals and enhances the Raman signal from the sample.

The sample holder schematics in FIG. 1B, C show that a single solid sample can also be extended to form a well plate array capable of containing multiple solid samples. An electropolished stainless steel well plate, as one example, is shown in FIG. 2. The benefits of using this well plate to enhance the Raman signal and simultaneously reducing the unwanted Raman background signals was published by A. Ryder et al[6]. A gold coating is preferred at 785 nm as it will significantly increase the reflectivity from around 35% for stainless steel to over 90% for a gold coating.

Figure 3A:
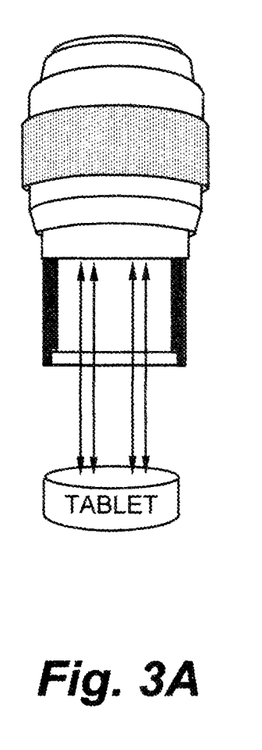
FIG. 3A shows collimated laser input and collimated Raman backscatter collection with an integrated Raman Calibration Standard (e.g., $CaF_2$) for Real-Time wavenumber calibration by wavenumber stamping each collected Raman spectra with the Raman band from the calibration standard (321.0 wavenumbers for CaF2)
Figure 3B:
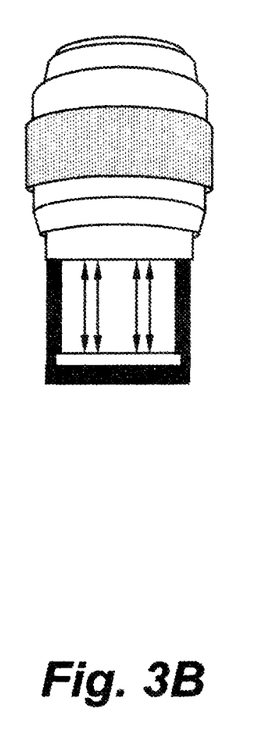
FIG. 3B is a schematic microscope objective accessory with an enclosed Raman Calibration Standard for wavenumber calibration.
Figure 3C:
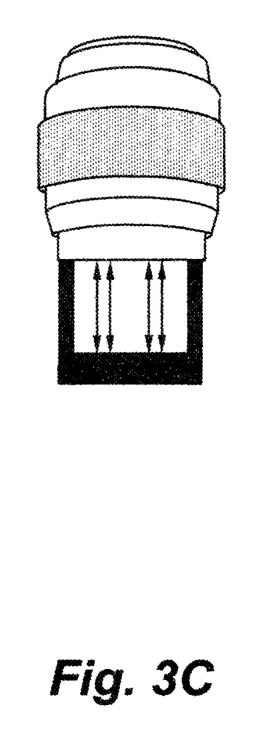
FIG. 3C is a schematic microscope objective accessory with enclosed NIST SRM 2241 Standard optic for Relative Intensity Corrections at 785 nm.

FIG. 3A shows the collimated laser input and collimated Raman backscatter collection with an integrated Raman Calibration Standard (e.g., $CaF_2$) for Real-Time wavenumber calibration by wavenumber stamping each collected Raman spectra with the Raman band from the calibration standard (321.0 wavenumbers for $CaF_2$). FIG. 3B is a schematic showing Microscope objective accessory with enclosed Raman Calibration Standard for wavenumber calibration. FIG. 3C is a schematic showing Microscope objective accessory with enclosed NIST SRM 2241 Standard optic for Relative Intensity Corrections at 785 nm.

Enclosing the Raman wavenumber calibration accessory and a NIST intensity calibration accessory benefit from using a collimated laser beam to generate representative Raman and Fluorescence signals while eliminating the problem of unwanted stray light and improving the placement accuracy of both types of reference optic with respect to the incident laser beam. All three objectives can be located on the same microscope objective turret so that they can be easily accessed when required by the experiment.

EXAMPLES

Figure 4:
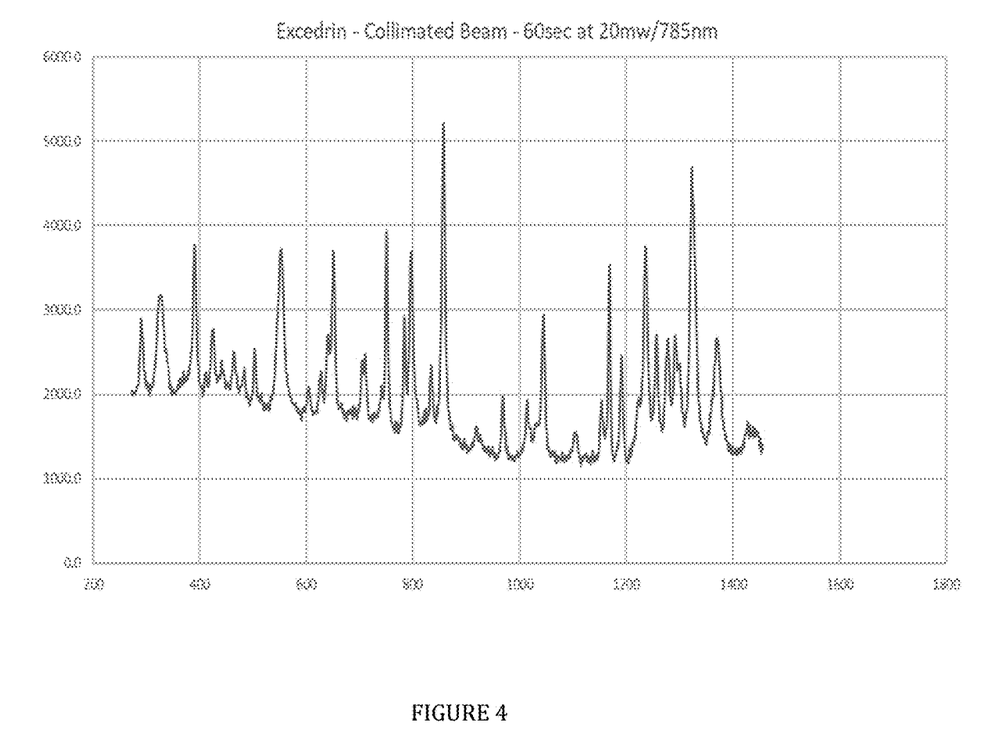
FIG. 4 is a plot of Raman spectra collected from over-the-counter generic Excedrin tablet using the collimated backscatter configuration as per FIG. 1A.

A microscope objective was removed from a Raman microscope to generate the collimated laser output beam and collimated backscatter collection. In FIG. 4, the high-quality Raman spectrum was collected from an over-the-counter generic Excedrin tablet using only the collimated backscatter configuration as per FIG. 1A.

Figure 5:
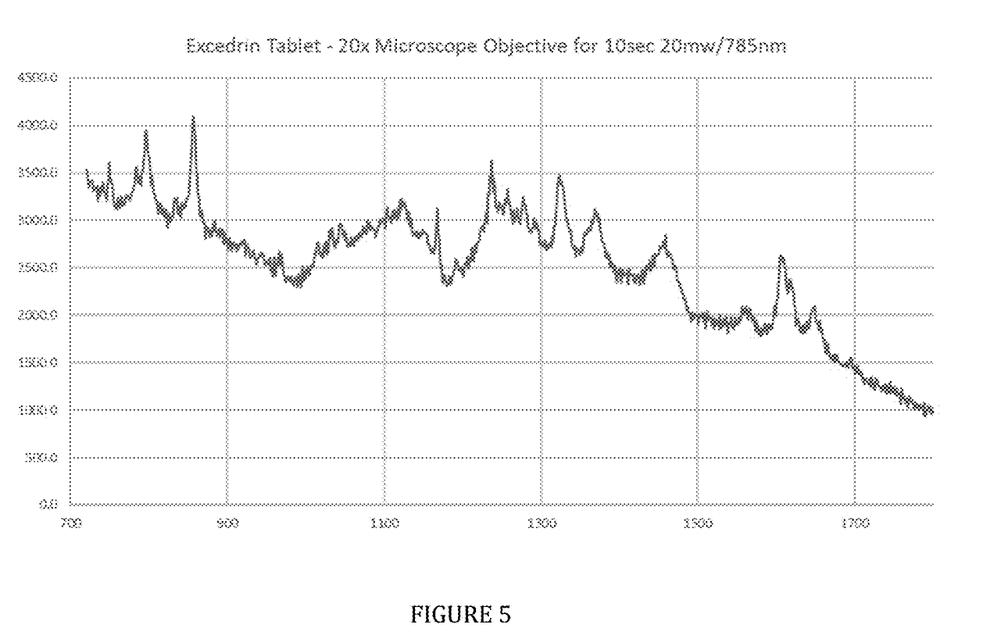
FIG. 5 shows the Raman spectra collected from the over-the-counter generic Excedrin tablet using a conventional Raman microscope with a 20× objective.

In FIG. 5, the Raman spectrum was collected from the same Excedrin tablet using the Raman microscope equipped with a 20× objective, due to the strong surface bias generated by using a focusing optic fluorescence from the surface coating strongly interferes with bulk Raman spectrum degrading the quality of the Raman spectrum.

Figure 6:
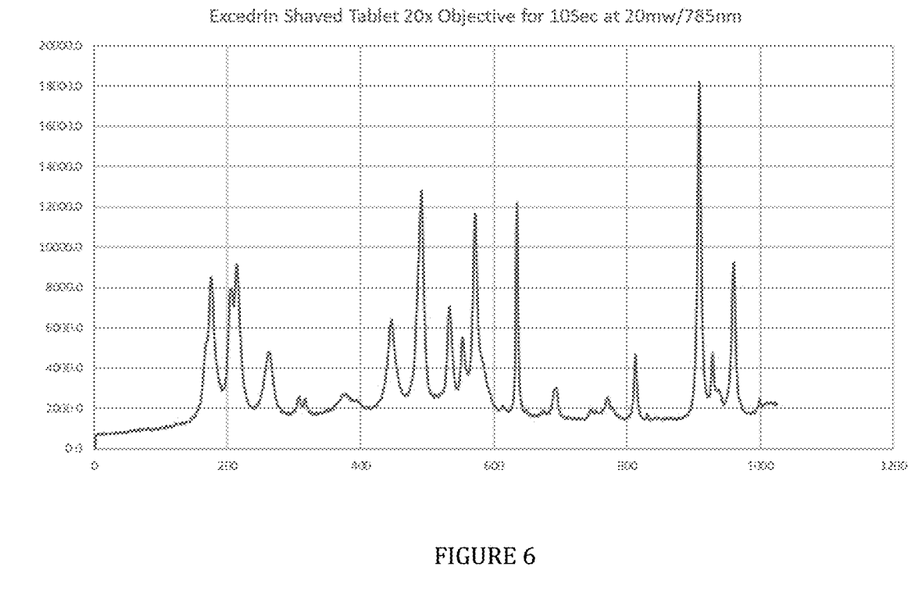
FIG. 6 illustrates the Raman spectra collected from a shaved over-the-counter Excedrin tablet using a conventional Raman microscope with a 20× objective.

To determine the impact of the surface coating on the Raman spectrum from the tablet, the surface coating was removed by shaving the tablet. FIG. 6 shows the Raman spectra collected from over the counter shaved Excedrin tablet using a conventional Raman microscope with a 20X objective. FIG. 6 demonstrates that by shaving the tablet, the unwanted fluorescence interference shown in FIG. 4 from the surface coating was removed, and a high-quality Raman spectrum was collected.

Figure 7:
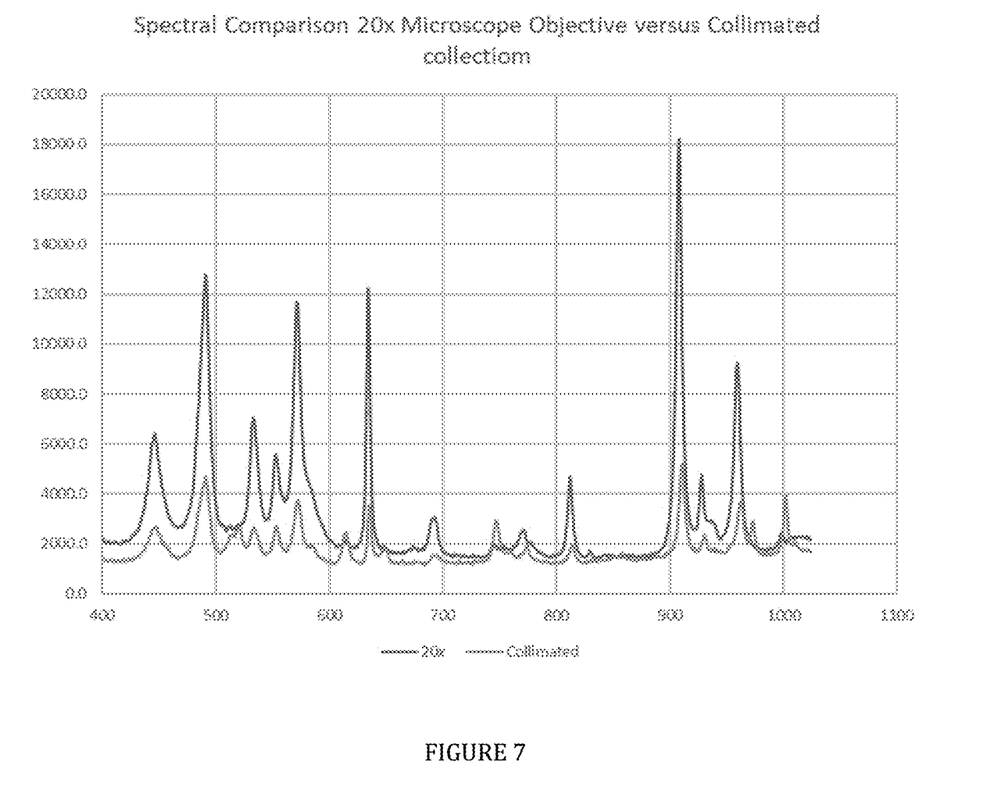
FIG. 7 superimposes the Raman spectra from FIG. 4 collected by the collimated backscatter configuration and the Raman spectra from FIG. 6 collected from the shaved tablet using a standard focusing microscope configuration.

FIG. 7 superimposes the Raman spectra from FIG. 4 collected by the collimated backscatter configuration and the Raman spectra from FIG. 6 collected from the shaved tablet using a standard focusing microscope configuration. The tablet contains three components, and the additional Raman bands are present within the spectra from FIG. 4 indicates that more representative sampling of the tablet by using the collimated light configuration was demonstrated. Enclosing the samples within a sample holder having a highly reflecting inner surface will redirect the laser by reflection back into the sample to enhance the Raman signal as described by Ryder[6].

REFERENCES

1. Johansson, J., Pettersson, S., Folestad, S., "Characterization of different laser irradiation methods for quantitative Raman tablet assessment" Journal of Pharm. and Bio. Anal. 2005, Vol. 39
2. U.S. Pat. No. 7,148,963, Dec. 12, 2006, Owen et al, Large-Collection-Area Optical Probe
3. Kleinebudde, P., Müller, J., "Validation of Raman spectroscopic procedures in agreement with ICH guideline Q2 with considering the transfer to real time monitoring of an active coating process" Journal of Pharm. and Bio. Anal. 2010. Vol. 53
4. Matousek, P., Parker, A. W., "Bulk Raman Analysis of Pharmaceutical Tablets", Applied. Spectroscopy 2006, Volume 60
5. U.S. Pat. No. 8,085,396, Dec. 27, 2011, Matousek et al, Raman Analysis
6. Ryder, A., et al, "A Stainless-Steel Multi-Well Plate (SS-MWP) for High-Throughput Raman Analysis of Dilute Solutions", Journal of Raman Spectroscopy 2010

The invention claimed is:

1. A method of performing Raman analysis of a solid sample, including a diffusively scattering solid sample, comprising the steps of:
    directing a collimated laser excitation beam directly onto a solid sample so as to induce from the sample a backscattered collimated collection beam;
    wherein the collimated laser excitation beam and the collimated collection beam follow a counter-propagating collimated optical path directly to and from the surface of the sample without any focusing or recollimation; and
    directing the collection beam to a spectrograph for Raman analysis of the sample.

2. The method of claim 1, wherein the collimated laser excitation beam is smaller in diameter than the collimated collection beam.

3. The method of claim 1, including the step of positioning a Raman calibration material in the collimated optical path.

4. The method of claim 3, wherein the Raman calibration material is a $CaF_2$ wavenumber calibration standard.

5. The method of claim 3, wherein the Raman calibration material is a NIST standard used for intensity calibration.

6. The method of claim 1, further including the step of supporting the sample in a reflective holder.

7. The method of claim 6, wherein the reflective holder is at least partially spherical.

8. The method of claim 6, wherein the reflective holder forms part of a multi-well plate.

9. The method of claim 1, wherein the counter-propagating collimated optical path is contained within a Raman microscope.

10. The method of claim 9, wherein:
    the Raman microscope includes an objective; and
    the objective is removed to enable the counter-propagating collimated optical path to extend directly to and from the surface of the sample.

11. The method of claim 10, wherein the objective is replaced with a window or calibration material.

12. The method of claim 1, wherein the sample is a pharmaceutical tablet, capsule, gelcap, coated pharmaceutical product, or packaged pharmaceutical product.

13. The method of claim 11, wherein the method is used to determine one or more of the following:
   a dosage formulation, properties of the pharmaceutical in polymorph form, hydrated form, solvate form, or salt form, and
   a highly absorbent or thick pharmaceutical dosage.

14. Apparatus for performing Raman analysis of a solid sample, including a diffusively scattering solid sample, comprising:
   a source of a collimated laser excitation beam; and
   optical apparatus operative to perform the following functions:
      directing the collimated laser excitation beam onto the solid sample so as to induce from the sample a backscattered collimated collection beam, such that the collimated laser excitation beam and the collimated collection beam follow a counter-propagating collimated optical path directly to and from the surface of the sample without any focusing or recollimation, and
      deliver the collection beam to a spectrograph to performing a Raman analysis of the sample.

15. The apparatus of claim 14, wherein the collimated laser excitation beam is smaller in diameter than the collimated collection beam.

16. The apparatus of claim 14, further including a Raman calibration standard positioned in the collimated optical path.

17. The apparatus of claim 16, wherein the Raman calibration standard is a $CaF_2$ wavenumber calibration standard.

18. The apparatus of claim 16, wherein the Raman calibration standard is a NIST intensity calibration standard.

19. The apparatus of claim 14, further including a sample holder with a reflective surface.

20. The apparatus of claim 19, wherein the sample holder is at least partially spherical.

21. The apparatus of claim 19, wherein the reflective holder forms part of a multi-well plate.

22. The apparatus of claim 14, wherein the counter-propagating collimated optical path forms part of a Raman microscope.

23. The apparatus of claim 16, wherein the sample is a pharmaceutical tablet, capsule, gelcap, a coated pharmaceutical product, or a packaged pharmaceutical product.

* * * * *